United States Patent [19]

Pies et al.

[11] Patent Number: 5,545,779
[45] Date of Patent: Aug. 13, 1996

[54] PROCESS FOR THE HYDRODEHALOGENATION OF HALOGENATED BENZENES

[75] Inventors: Michael Pies, Duisburg; Josef Käsbauer, Wermelskirchen; Helmut Fiege, Leverkusen, all of Germany

[73] Assignee: Bayer Aktiengesellschaft, Leverkusen, Germany

[21] Appl. No.: 319,397

[22] Filed: Oct. 6, 1994

[30] Foreign Application Priority Data

Oct. 13, 1993 [DE] Germany .......................... 43 34 792.4

[51] Int. Cl.⁶ ...................................... C07C 17/00
[52] U.S. Cl. ...................................... 570/204
[58] Field of Search ............................... 570/204

[56] References Cited

U.S. PATENT DOCUMENTS

| 2,726,271 | 12/1955 | Troyan et al. | 570/204 |
|---|---|---|---|
| 2,826,617 | 3/1958 | Redman et al. | 570/204 |
| 2,866,828 | 12/1958 | Crowder et al. | 570/204 |
| 2,943,114 | 6/1960 | Redman et al. | 570/204 |
| 2,949,491 | 8/1960 | Rucker | 570/204 |
| 3,054,830 | 9/1962 | Luvisi et al. | 210/204 |
| 4,827,057 | 5/1989 | Kasbauer et al. | 520/204 |

FOREIGN PATENT DOCUMENTS

| 0301343 | 2/1989 | European Pat. Off. | 570/204 |

OTHER PUBLICATIONS

114: 121703n, M. Uhlir et al, "Catalytic hydrogenolysis of hexachloro–benzene to lower–chlorinated benzenes"; Chem. Abstrs., v 114, 1991, p. 732.

Ullmann's Encyclopedia of Industrial Chemistry, vol. A8; "Cyclohexane", pp. 211–213 + cover page and back page, W. Gerhartz.

*Primary Examiner*—Samuel Barts
*Attorney, Agent, or Firm*—William C. Gerstenzang; Sprung Horn Kramer & Woods

[57] ABSTRACT

Halogenated benzenes are hydrodehalogenated in a particularly advantageous manner and at low temperatures by contacting them at temperatures of between 100° and 250° C. together with hydrogen with a catalyst prepared by application of one or more salts of palladium and/or platinum and, if desired, of copper to an alumina or titanium dioxide support.

10 Claims, No Drawings

PROCESS FOR THE HYDRODEHALOGENATION OF HALOGENATED BENZENES

The present invention relates to a process for the hydrodehalogenation of halogenated benzenes by reation with hydrogen in the presence of a catalyst.

Halogenation of benzene often also produces halogenation products which are of little industrial and economic interest due to the fact that step and isomer selectivities are less than 100%. Preparation of dichlorobenzene often results, for example, in the formation of substantial amounts of the p isomer and trichlorobenzenes as surplus products in addition to the desired o and m isomers. Processes for converting such surplus products into the starting material benzene and a valuable intermediate (monochlorobenzene) are already known. The same is also true of 1,2,4-trichlorobenzene, which can be converted into the valuable products o-dichlorobenzene and monochlorobenzene. Corresponding hydrodehalogenations are also known for benzenes having an even higher degree of chlorination.

Thus, U.S. Pat. No. 2,826,617 describes the reaction of tetrachlorobenzene with hydrogen over a palladium/alumina catalyst. The reaction temperatures given are 300° to 400° C. and are thus very high for industrial implementation. According to U.S. Pat. No. 2,943,114, a titanium dioxide catalyst impregnated with copper(I) chloride only gives about 50% conversion of the starting material in a similar process despite reaction temperatures of 300° to 500° C. U.S. Pat. Nos. 2,866,828 and 2,886,605 describe the use of copper(I) chloride on alumina for such purposes. The short-term tests described there also lead to the desired hydrodehalogenation products only if the temperatures are as high as 350° to 375° C. The same is true of the platinum/spinel catalysts listed in EP-A10,301,343. Neither has hydrodechlorination of trichlorobenzene with the addition of ammonium acetate (U.S. Pat. No. 3,054,830) gained any industrial importance since it also requires, in addition to the high reaction temperatures of about 300° C., high pressures of more than 100 bar.

For thermodynamic reasons, there is a prejudice against carrying out hydrodehalogenations of halogenated benzenes in which the aromatic ring is maintained at temperatures below 300° C. The reason for this is that hydrogenation of the aromatic ring to give cyclohexane derivatives must be expected at such temperatures since cyclohexane is usually prepared by hydrogenation of benzene at temperatures below 300° C. (see Ullmann's Encyclopedia of Industrial Chemistry, 5th Edition, Volume A8, page 211 (1987)).

Accordingly, there is still a need for a process which converts aromatics having a fairly high degree of halogenation into valuable substances having a low degree of halogenation and/or into benzene under mild reaction conditions and at a high degree of conversion and in which no appreciable formation of cyclohexane derivatives takes place.

A process for the hydrodehalogenation of halogenated benzenes of the formula (I)

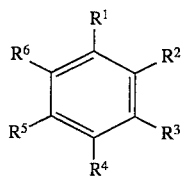

(I)

in which the radicals $R^1$ to $R^6$, independently of one another, represent hydrogen or halogen, but at least two of these radicals represent halogen, has now been found, which process is characterized in that halogenated benzenes of the formula (I) are contacted at temperatures of between 100° and 250° C. together with hydrogen with a catalyst prepared by application of one or more salts of palladium and/or platinum and, if desired, of a copper salt to an alumina or titanium dioxide support.

In as far as $R^1$ to $R^6$ in formula (I) are halogen, they can be, for example, chlorine, bromine or iodine. They are preferably chlorine. The materials used in the process according to the invention are in particular 1,4-dichlorobenzene, 1,2,3-, 1,2,4- and 1,3,5-trichlorobenzene and 1,2,3,4-, 1,2,3,5- and 1,2,4,5-tetrachlorobenzene. It is of course also possible to use mixtures of different halogenated benzenes.

The preferred temperatures for the process according to the invention are those ranging from 150° to 250° C.

Hydrogen can be used in the process according to the invention in the customary grades. For example, 0.5 to 50 mol of hydrogen can be used per mole of halogen in the halogenated benzene used. This amount is preferably 1 to 30 mol.

The hydrogen can also be used in a mixture with an inert gas, for example nitrogen. The hydrogen content of such mixtures can be, for example, 10 to 50% by volume. If hydrogen/inert gas mixtures are used, at least 1 mol of hydrogen is generally used per mole of halogen in the halogenated benzene.

The catalyst has been prepared by application of palladium salts and/or platinum salts and, if desired, copper salts to an alumina or titanium dioxide support. The salts can be, for example, $PdCl_2$, $PtCl_2$, $PtCl_4$, $CuCl$ or $CuCl_2$, and the supports can be customary, preferably particulate, $Al_2O_3$ or $TiO_2$ types such as customary for the preparation of supported catalysts. Preference is given to catalysts prepared from palladium salts and, if desired, copper salts and supports having a mean particle size of 1 to 6 mm and a BET surface area of more than 150 $m^2/g$.

The salts can be applied to the supports by customary methods, for example by impregnating the support with a solution of the salts, followed by drying or calcining. For example, 0.5 to 100 g, preferably 1 to 50 g, of salts can have been applied to the catalysts per liter. Salts applied to the support can, if desired, be reduced prior to or during the hydrodechlorination according to this invention.

For example, 0.5 to 5 mol of halogenated benzenes can be passed over the catalyst per hour and per liter of catalyst. This amount is preferably 1 to 3 mol per hour and liter of catalyst. If desired, the process according to this invention can also be carried out batchwise but is preferably carried out continuously.

Preferred pressures for the process according to this invention are those ranging from 1 to 5 bar. Pressure and reaction temperature are preferably combined in such a manner that the halogenated benzenes of the formula (I) used make contact with the catalyst in gaseous form.

The reaction mixture leaving the reactor can, for example, be used in such a manner that, if necessary, it is cooled and again fed into a chlorination reaction. If, for example, 1,4-dichlorobenzene which has been separated from the reaction mixture of a benzene dichlorination as undesirable by-product is used in the process according to the invention, a hydrodehalogenation mixture is obtained in which only a small amount of 1,4-dichlorobenzene is left. If this hydrodehalogenation mixture is fed into a chlorination process for preparing dichlorobenzene together with benzene and/or monochlorobenzene, the reformation of 1,4-dichlorobenzene in the chlorination process is reduced.

The mixture leaving the reactor can also be cooled and separated into its components by distillation or by a different method, and these components may be further used individually.

The process according to this invention makes it possible to hydrodehalogenate halogenated benzenes at industrially advantageous low temperatures while giving high conversions and selectivities and, if desired, high gas-flow rates and thus reaction temperatures which are easy to control. With respect to the prior art described at the beginning, it is particularly surprising that in the process according to the invention cyclohexane derivatives are formed, if at all, only in traces.

EXAMPLES

Catalyst A

This catalyst is a titanium dioxide extrudate of dimensions 2.5 mm in diameter and 8 mm in length which has been coated with 40 g of $PdCl_2$ per liter by impregnation.

Catalyst B

This catalyst consists of alumina beads (mean diameter 3 mm) which have been coated with 40 g of $PdCl_2$ and 10 g of $CuCl_2$ per liter by impregnation.

Catalyst C

This catalyst consists of the same $Al_2O_3$ beads as catalyst B, except that they have been coated with 40 g of $CuCl_2$ per liter by impregnation. This catalyst is used for comparison.

Example 1

60 g of catalyst A were introduced between two beds of quartz cullet particles (mean size 3 mm) in a reaction tube 700 mm in length and 17 mm in inner diameter and heated to 180° C. 25 g of 1,4-dichlorobenzene (weight hourly space velocity =0.4 $h^{-1}$) and 90 Nl of hydrogen per hour were then passed continuously over the catalyst from above. At the end of the reaction tube, the reaction mixture was cooled, condensed and collected in a separator. The composition of the reaction mixture can be seen from Table 1 below.

Example 2

The procedure of Example 1 was repeated, except that only 30 g of catalyst A were used and 15 g of 1,4-dichlorobenzene (weight hourly space velocity =0.5 $h^{-1}$) and 70 Nl of hydrogen per hour were passed over the catalyst. The experiment was carried out over a period of 250 hours, during which virtually no change occurred in the composition of the reaction mixture (see Table 1 below).

Example 3

The procedure of Example 1 was repeated, except that 12 g of 1,2,4-trichlorobenzene and 5 Nl of hydrogen per hour were continuously passed over the catalyst at 210° C. instead of 1,4-dichlorobenzene. The composition of the reaction mixture which essentially contained 1,2-dichlorobenzene and monochlorobenzene was determined after an experiment time of 180 hours and can be seen from Table 1 below. The conversion after an experiment time of 180 hours was still 97.9%.

Example 4

The procedure of Example 3 was repeated, except that the reaction was carried out at 180° C. and 7.5 l of hydrogen per hour were introduced. After an experiment time of 200 hours, the conversion was still 84.2%. The composition of the reaction mixture after an experiment time of 200 hours can be seen from Table 1 below. The reaction product contained essentially 1,2- and 1,3-dichlorobenzene and monochlorobenzene.

Example 5

The procedure of Example 3 was repeated, except that 25 g of 1,3,5-trichlorobenzene were continuously hydrodechlorinated at 250° C. per hour with 5 Nl of hydrogen. At a conversion of about 50%, 1,3-dichlorobenzene was formed at a selectivity of 80%. The detailed composition of the reaction product can be seen from Table 1 below.

Example 6

The procedure of Example 1 was repeated, except that 60 g of catalyst B were used, to which 24 g of 1,4-dichlorobenzene and a mixture of 8 Nl of hydrogen and 14.5 Nl of nitrogen were applied per hour at a pressure of 3 bar. After an experiment time of 1000 hours, the conversion was still 74.6%. Here, too, virtually the only reaction products obtained were benzene and monochlorobenzene. Details can be seen from Table 1 below.

Example 7 (for comparison)

The procedure of Example 1 was repeated, except that 40 g of 1,4-dichlorobenzene and 35 Nl of hydrogen were passed at 200° C. per hour over 60 g of catalyst C. The reaction mixture collected contained 0.1% by weight of monochlorobenzene and otherwise only unconverted starting material.

Example 8 (for comparison)

The procedure of Example 1 was repeated, except that 30 g of 1,4-dichlorobenzene and 45 Nl of hydrogen were passed at 60° C. per hour over 129 g of catalyst B. The reaction product consisted virtually exclusively of cyclohexane.

TABLE 1

| | | | Reaction mixture (% by weight) | | | | | | | |
|---|---|---|---|---|---|---|---|---|---|---|
| | Tempera- | | Cyclo- | Ben- | Mono-chloro- | Dichlorobenzene | | | Trichloro-benzene | |
| Ex. No. | ture (°C.) | Material used *) | hexane | zene | benzene | 1,2- | 1,3- | 1,4- | 1,2,4- | 1,3,5- |
| 1 | 180 | 1,4-DCB | <0.1 | 46.1 | 46.1 | — | — | 7.4 | — | — |
| 2 | 180 | 1,4-DCB | <0.1 | 32.5 | 55.7 | — | — | 11.7 | — | — |
| 3 | 210 | 1,2,4-TCB | <0.1 | 9.0 | 40.4 | 38.7 | 5.6 | 4.1 | 2.1 | — |
| 4 | 180 | 1,2,4-TCB | <0.1 | 1.8 | 20.4 | 44.1 | 10.3 | 7.5 | 15.8 | — |
| 5 | 250 | 1,3,5-TCB | <0.1 | 0.5 | 8.3 | — | 39.5 | — | — | 49.2 |
| 6 | 180 | 1,4-DCB | <0.1 | 50.8 | 23.6 | — | — | 25.4 | — | — |
| 7**) | 200 | 1,4-DCB | <0.1 | — | 0.1 | — | — | 99.9 | — | — |
| 8**) | 60 | 1,4-DCB | 97.5 | 2.3 | 0.1 | — | — | 0.1 | — | — |

*)DCB = Dichlorobenzene, TCB = Trichlorobenzene
**)Comparative examples

What is claimed is:

1. A process for the dechlorination of one or more chlorinated benzenes selected from the group consisting of 1,4-dichlorobenzene, 1,2,3-, 1,2,4- and 1,3,5-trichlorobenzene and 1,2,3,4- 1,2,3,5- and 1,2,4,5-tetrachlorobenzene to form one or more benzenes having a lower degree of chlorination than said one or more chlorinated benzenes, which comprises contacting said one or more chlorinated benzenes with hydrogen in the presence of a catalyst prepared by applying $PdCl_2$, $PtCl_2$, $PtCl_4$ or a combination thereof to an aluminum or titanium dioxide support, at a temperature of 100° to 250° C.

2. The process of claim 1, in which additionally a copper salt is applied to the support.

3. The process of claim 1, in which a chlorinated benzene of the formula (I) is used in which at least two of the radicals $R^1$ to $R^6$ represent chlorine.

4. The process of claim 1, is carried out at 150° to 250° C.

5. The process of claim 1, in which 0.5 to 50 mol of hydrogen are used per mole of halogen in the chlorinated benzene used.

6. The process of claim 1, in which the hydrogen is used in a mixture with an inert gas.

7. The process of claim 1, in which the catalyst has been prepared by additional application of CuCl or $CuCl_2$.

8. The process of claim 1, in which 0.5 to 100 g of salt have been applied to the catalyst per liter.

9. The process of claim 1, which is carried out at pressures ranging from 1 to 5 bar and in the gas phase.

10. The process of claim 1 in which the mixture present after the reaction is fed into a chlorination reaction.

* * * * *